United States Patent [19]

Markling

[11] 4,321,226
[45] Mar. 23, 1982

[54] METHOD AND APPARATUS FOR MAKING TUBULAR PRODUCTS SUCH AS CATHETERS

[75] Inventor: Jørgen Markling, Ballerup, Denmark
[73] Assignee: A/S Surgimed, Ølstykke, Denmark
[21] Appl. No.: 121,682
[22] Filed: Feb. 15, 1980
[30] Foreign Application Priority Data Feb. 19, 1979 [DK] Denmark ................................. 717/79

[51] Int. Cl.³ ..................... B29C 17/08; B29D 3/02; B29D 23/04; B29D 23/05
[52] U.S. Cl. ................................... 264/139; 29/460; 264/149; 264/150; 264/151; 264/163; 264/172; 264/173; 264/255
[58] Field of Search .............. 264/139, 148, 149, 150, 264/159, 162, 165, 171, 173, 174, 209.3, 255, 250, 296, 334, 103, 285, 339, 163, 172, 151; 29/460

[56] References Cited

U.S. PATENT DOCUMENTS

| | | | |
|---|---|---|---|
| 2,043,630 | 6/1936 | Raiche | 264/250 |
| 2,086,654 | 7/1937 | Winder | 264/250 |
| 2,248,934 | 7/1941 | Auzin | 264/250 |
| 2,259,488 | 10/1941 | Raiche | 264/334 |
| 2,330,399 | 9/1943 | Winder | 264/250 |
| 2,585,707 | 12/1952 | Stevens | 264/173 |
| 3,359,357 | 12/1967 | Bently et al. | 264/173 |
| 3,988,189 | 10/1976 | Sullivan | 264/103 |
| 4,115,495 | 9/1978 | Hartitz | 264/159 |
| 4,210,478 | 7/1980 | Shoney | 264/250 |
| 4,219,522 | 8/1980 | Oyama | 264/173 |

FOREIGN PATENT DOCUMENTS

| | | | |
|---|---|---|---|
| 703849 | 2/1965 | Canada | 264/281 |
| 51-12072 | 10/1972 | Japan | 264/173 |
| 134060 | 12/1951 | Sweden | 264/173 |
| 977208 | 12/1964 | United Kingdom | 264/173 |

*Primary Examiner*—Willard E. Hoag
*Attorney, Agent, or Firm*—Fleit & Jacobson

[57] ABSTRACT

Tubular products are provided by applying a first, inner plastic layer onto a core wire and by applying a wire sheathing onto the first plastic layer as a continuous structure thereon. The wire sheathing is then locally removed to provide defined, spaced areas without wire sheathing and intermediate areas including the wire sheathing, and the structure thus provided is covered by applying a second, outer plastic layer thereon, thereby providing a strand structure. As a next step, this strand structure is cut at one limitation of each area without wire sheathing, whereby strand pieces are provided having one end portion which has no wire sheathing therein. The core wire piece left in each strand piece is then removed, thereby providing a tubular product having a body portion including wire sheathing and being completely integral with an end or tip portion without wire sheathing. Due to the complete lack of discontinuity between body portion and tip portion, the tubular products are very suited for use as reliable catheters, and to that end the tip portion can be appropriately formed as needed.

6 Claims, 4 Drawing Figures

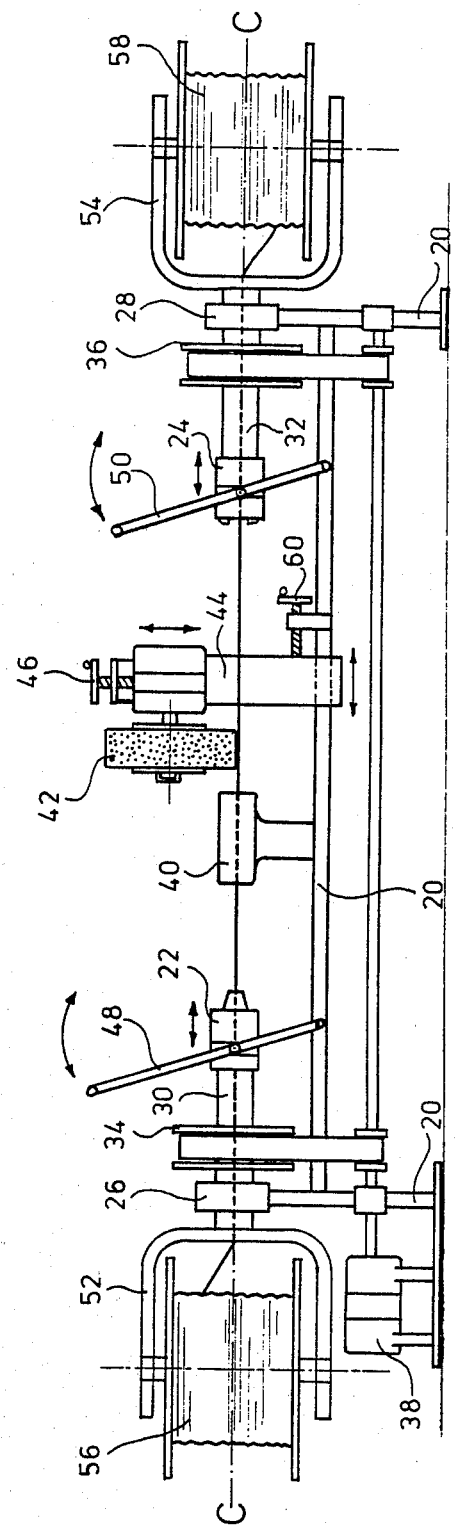

METHOD AND APPARATUS FOR MAKING TUBULAR PRODUCTS SUCH AS CATHETERS

BACKGROUND OF THE INVENTION

The present invention relates to the manufacture of tubular products, particularly useful as or for preparing an improved catheter construction. Catheters of the type contemplated are relatively thin and flexible tubes which include inner and outer plastic layers and a wire sheathing embedded therebetween. Generally, the wire sheathing is braided or cross-wound in order to obtain maximum torsional rigidity and a good longitudinal flexibility.

When inserting such a catheter, for instance in a vein, these properties are dicisive, since an easy and reliable insertion will imply firstly that the catheter is able to follow and adapt to the shape of the vein and secondly that the catheter can be rotated about its own axis without being torsionally deformed thereby.

With a view to the insertion, catheters generally also include a hollow plastic tip or distal end in which the wire sheathing has been omitted in order to render the tip more flexible than the remaining part of the catheter.

Previously, the manufacture of such catheters with a flexible plastic tip has been difficult, since the omission of the wire sheathing in the tip or distal end has complicated the manufacture. It is known to prepare catheters of the type contemplated two parts, viz. a tubular body portion with wire sheathing and a separate tip portion without wire sheathing therein.

The body portion is prepared by extruding a first plastic layer onto a core wire, whereafter a relatively tight-fitting wire braid is applied onto this first plastic layer and then a second or outer plastic layer is applied also by extrusion. Finally, pieces of appropriate length are cut from the strand product thus prepared.

Thereafter, or in parallel therewith, tip portions are prepared separately, for instance by extruding a plastic layer having the necessary thickness onto a core wire having the same diameter, and by cutting appropriate pieces therefrom.

Thereafter, a tip portion must be joined to a body portion and this is performed by removing the outer plastic layer on the body portion in such a manner that a portion of the wire braid therein is exposed at one end of the body portion. Thereafter the plastic tip is slipped over the exposed wire braid on the body portion and this will necessitate that one end of the tip portion is expanded in advance by means of a particular tool. Finally, the plastic materials of the end portions thus slipped one over the other are welded or fused together which requires supply of heat and, moreover, pressure must be exerted exteriorly over the joint in order to ensure a completely smooth outer surface.

This way of manufacture is very complicated and time consuming not only due to the necessary joining, but also due to the factthat it is necessary to prepare and handle small pieces separately, namely a tip portion and a body portion for each catheter to be prepared.

Another essential drawback consists in that faulty or incomplete joints are difficult to avoid completely, even with a very careful and comprehensive product control and testing. If such faulty products are to be excluded with an absolute certainty, the check measures necessary to that end will cause a further increase in the product costs.

It is an object of the invention to provide an improved technique whereby tubular products, in particular catheters of the type contemplated can be prepared with substantially lower production costs, with high certainty of faultless products and with a low rejection percentage during the manufacture.

Other objects and advantages of the present invention will become apparent as the description proceeds.

SUMMARY OF THE INVENTION

In one aspect, the present invention provides a method of preparing a tubular product, in particular for making catheters, the tubular product including an inner plastic layer, and outer plastic layer and a wire sheathing embedded therebetween. The method comprises the steps of applying the inner plastic layer onto a core wire as a plastic coating thereon; applying the wire sheathing onto the plastic coating as a continuous structure thereon; locally removing the wire sheathing at spaced locations, thereby providing defined spaced circumferential areas without wire sheathing thereon and intermediate areas including the wire sheathing; applying the outer plastic layer over the spaced and intermediate areas, thereby providing a strand structure covered by the outer plastic layer; cutting the strand structure at the region of one limitation of each of the defined spaced areas without wire sheathing, thereby providing strand pieces, one end portion of each strand piece being without wire sheathing; and removing the core wire from the strand pieces to provide the tubular product.

The entire method may be performed on a continuous production line and, if necessary, means such as take up rollers for temporarily taking up the product can be arranged, e.g. before and after the location at which the local removal of the wire sheathing is carried out.

As an alternative, a reeling step can be performed subsequent to the step of applying the wire sheathing and such reels can be placed in an intermediate storage from which the reels can be transferred to the equipment for locally removing the wire sheathing. After this removing step, the product can go on to the equipment in which the step of applying the outer plastic layer is carried out or, alternatively, the product can be wound again onto reels after the step of locally removing the sheathing.

The steps of cutting the product into strand pieces and removing the core wire pieces therefrom can be performed either directly in continuation of the application of the outer plastic layer, or subsequent to a temporary storage and/or shipment on reels.

In the latter case, the strand structure provided and possibly temporarily stored on reels will be a very useful stock product, in particular for further processing into catheters. The strand structure comprises the core wire, the inner plastic layer thereon, the embedded wire sheathing which has been interrupted or removed at spaced locations, and the outer plastic layer which has a continuous and smooth outer surface. In another aspect, the present invention provides a method of manufacturing such an elongate stock product.

After the cutting step, the core wire piece left in each strand piece provided is removed, preferably by longitudinally stretching the core wire piece to such an extent that a permanent elongation with a corresponding contraction of the diameter occurs, thereby facilitating the removal or withdrawal of the core wire.

The tubular product thus provided is very useful as or for improved catheters, since there is no discontinuity in the plastic material at the transition between the area including wire sheathing and the area of end portion without any sheathing. As mentioned above, the methods of the invention can be carried out continuously to a wide extent and even if this is not performed, the various intermediate or strand products can conveniently be handled and transported on reels. Accordingly, it is not necessary to handle and not at all to join small pieces as is the case in accordance with the prior art mentioned above. Thus, the invention provides a substantially simpler manufacture with high product quality.

The invention also relates to an apparatus for use in performing the method and, more particularly, for use to carry out the local removal of the wire sheathing before the step of applying the outer plastic layer. By means of the apparatus, a length of the core wire having the inner plastic layer and the wire sheathing applied thereon can be clamped in a tensioned condition between the two clamping collets or chucks whereafter the wire sheathing can be ground away in a defined circumferential area of a desired size and than a new length can be pulled into the apparatus for treatment therein.

Finally, the invention also comprises a tubular product and an improved catheter construction provided in accordance with the teachings of the invention.

BRIEF DESCRIPTION OF THE DRAWINGS

FIG. 4 is a side view schematically illustrating an apparatus in accordance with the invention for locally grinding away the wire sheathing when performing the methods of the invention.

DETAILED DESCRIPTION OF ILLUSTRATIVE EMBODIMENTS

Figure 1:
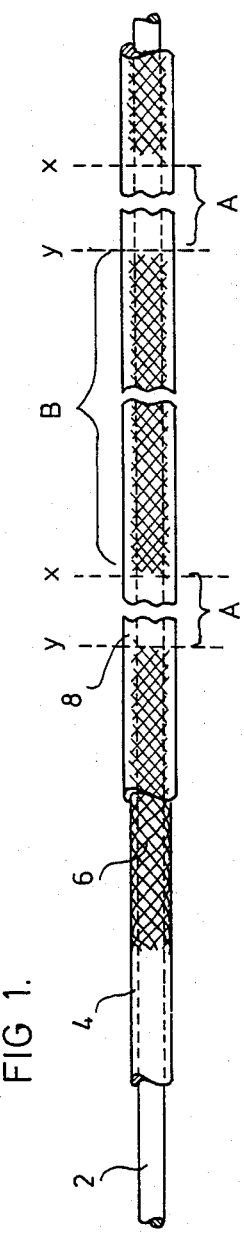
FIG. 1 is a partial schematic view in which portions have been broken away in order to show underlying structures and illustrating a segment of a strand product which can be considered as an intermediate product or as a stock product provided in accordance with the invention.

Reference is now made to the drawings, wherein FIG. 1 shows an example of a particular intermediate product or stock product which is produced when performing the method of the invention. A core wire 2, e.g. made of silver or stainless steel, has been coated exteriorly with a first plastic layer 4 and on this plastic layer there has been wound a wire sheathing 6 which may include e.g. 16 cross-wound individual wires of stainless steel. The plastic layer 4 and the wire sheathing 6 as well can be applied by use of conventional and well known techniques.

The wire sheathing 6 does not extend continuously throughout the product inasmuch as the sheathing has been interrupted or removed at spaced locations in areas A. The intermediate areas B include, on the other hand, the wire sheathing 6 and the transition areas are indicated at X and Y.

Moreover, the product comprises a second or outer plastic layer 8 which extends continuously and has a smooth outer surface. The outer plastic layer can also be applied by use of well known extrusion techniques. In the areas A without wire sheathing, the two plastic layers 4, 8 are joined directly, whereas the layers are joined through the interstices of the sheathing in the areas B. In FIG. 1, the wire sheathing 6 has been indicated schematically by cross-hatchings although covered by the outer layer and in the left portion of FIG. 1, the layers are shown separately. In the actual product, the outer layer 8 will of course extend continuously from end to end.

From an intermediate or stock product as that shown in FIG. 1, tubular products are prepared in accordance with the invention by appropriately cutting the product either at the transition areas X or at the transition areas Y so that separate pieces or lenghts are produced, each length including an area B with wire sheathing 6 and in continuation thereof an area A without wire sheathing.

This cutting or shearing can be performed manually or automatically, since the product of FIG. 1 e.g. can be moved through or past an inductive detector which responds to the presence or to the absence of the metal wire sheathing and thereby is able to control and operate e.g. a shearing machine.

Figure 2:
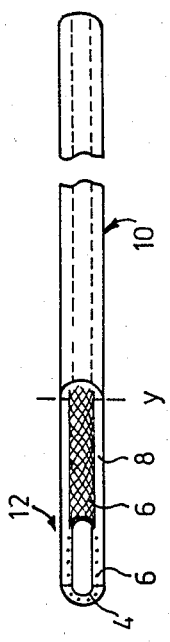
FIG. 2 is a partial schematic view in which portions have been broken away and illustrating a tubular product prepared in accordance with the invention and shown partially in section.

After the cutting step, the core wire pieces are removed and the result will be a product similar to that indicated in FIG. 2.

Such a tubular product includes in other words a body portion 12 including wire sheathing 6 and a distal end or tip portion 10 without any sheathing. In FIG. 2, the body portion 12 is shown partially in section and strongly shortened. The actual length of the body portion will depend on the application contemplated, but generally the body portion will be substantially longer than the distal end 10. The length of the distal end can e.g. be about 150 mm. The inner diameter of the product which has been determined by the outer diameter of the core wire used can e.g. be 1.0–1.5 mm, whereas the outer diameter of the product e.g. may be 2.0–2.6 mm. The plastic materials of the two layers 4, 8 may e.g. be polyethylene or polyurethane elastomers.

A tubular product as that shown in FIG. 2 is very suitable as a catheter, since the wire sheathing 6 provides a high degree of torsional control during the catheter insertion, whereby the catheter is manipulated from its proximal end. The distal end 10 of the catheter is completely integral with the body portion 12 and, accordingly there is no risk that the distal end or tip portion may break off during the catheterization.

However, a tubular product as that shown in FIG. 2 will also be suitable for other applications, since the product is a flexible high strength plastic tubing having an extremely accurately prepared inner bore.

Figure 3:
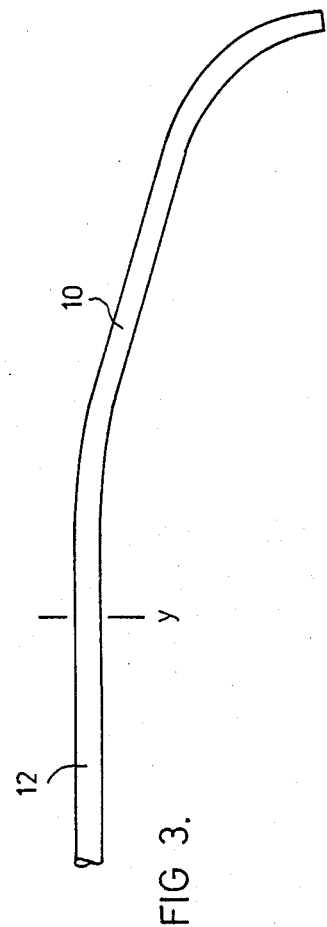
FIG. 3 is a schematic view of a segment of a tubular product prepared in accordance with the invention and shaped as a catheter provided with a curved and slightly tapered tip portion or distal end.

FIG. 3 shows an example of a tubular product prepared in accordance with the invention and specifically formed as a catheter. The distal end 10 of the catheter has been somewhat tapered and has, moreover, been provided with a permanent curvature, whereby the catheter can be directed selectively, e.g. into a branch vein.

FIG. 4 shows schematically an embodiment of an apparatus for use in carrying out the local removal which is particular to the invention, of the wire sheathing 6 in the areas A.

At opposite ends of a machine frame 20, there are supported two clamping collets or chucks 22, 24, respectively, which are rotatably journaled in respective main bearings 26, 28, so that the two collets are confronting each other and are aligned along a main axis C—C. The collets are mounted on associated shafts 30, 32, respectively, which moreover carry respective belt pulleys 34, 36, by which the two collets can be powdered to rotate synchronously about the main axis C—C, for instance by means of a motor 38 with an associated tooth-belt drive.

Between the collets 22, 24, there is, moreover, mounted a guide or support sleeve 40 which is retained with a through-going guide opening therein being coaxial with the main axis C—C.

A grinding assembly such as a rotating grinding wheel 42 or a grinding belt, is supported in a mounting 44, whereby the grinding assembly is movable toward and away from the main axis C—C, e.g. by means of a screw spindle with a handwheel 46 similar to the transverse slide of a usual turning lathe. In FIG. 4, these movements are indicated in vertical direction, but the same movements may also take place in other directions.

The collets 22, 24, can be opened and closed and their respective shafts 30, 32 are hollow.

With the arrangement described, the core wire 2 with the plastic layer 4 applied thereon and the wound and yet continuous wire sheathing 6 can be threaded through the two collets while these are open and also through the guide opening of the support sleeve 40. Thereafter, the wire can be clamped in a tensioned condition between the closed collets, whereafter the grinding assembly 42 can be moved or adjusted to locally grind away the wire sheathing, whereas the underlying plastic layer is left intact as far as possible. During the grinding operation, the collets rotate and, accordingly, also the wire or strand section clamped and tensioned between the collets. During the grinding operation, this wire or strand section shall have to carry out at least one complete revolution about the main axis C—C. Subsequent to such grinding operation, a new strand section can be drawn into the apparatus and be tensioned between the collets 22 and 24.

The tensioning of the strand section in the apparatus can be carried out manually, but according to the invention it is preferred that at least one of the clamping collets is displaceable along the main axis between a first position wherein the collet is open and is advanced toward the other collet, and a second retracted position, wherein the collet is closed and can be locked in position.

In FIG. 4, such an axial displacement has been indicated schematically by means of arms 48, 50, the collet 22 being shown in its retracted and closed position, while collet 24 is shown in its advanced and open position. With this arrangement, the strand may be tensioned between the collets at the same time as one of the collets or both collets are retracted and closed.

As already mentioned, it is only necessary, at least in principle, that the clamped and tensioned strand section rotates a single revolution during the grinding operation. However, it is substantially more expedient and effective, if the clamped and tensioned strand section rotates several or even many revolutions during the grinding operation. In this connection it will be necessary to take particular measures in order to prevent that the strand portions outside of the clamping collets become disarranged or disordered during the rotation of the strand.

In FIG. 4 each of the two clamping collets is, therefore, provided with suspension or support means 52, 54, respectively, which rotate together with the collets and in which a reel 56, 58, respectively, can be inserted and supported rotatably about an axis at right angles to a plane which includes the main axis C—C. With this arrangement, the strand to be treated can be unreeled from one of the reels and thereby be drawn into the apparatus at the same time as a strand section already treated is wound onto the other reel. Thus, the two support means 52, 54, and the respective reels therein will rotate together with the clamping collet associated therewith, and the strand section tensioned between the collets will accordingly be able to rotate unobstructed during the grinding operation.

The support means 52 and 54 are shown to be bifurcated, but may also be closed frames, whereby an additional main bearing can be provided to support the frames during their rotation.

During the grinding operation, the extension or axial length of the areas wherein the wire sheathing is to be removed, can be determined by the width of the grinding means 42. However, in order to provide the possibility of removing the wire sheathing 6 in areas of different or variable extension along the strand, it may be expedient that the mounting or carriage of the grinding assembly also is displaceable along the main axis C—C as indicated schematically by a screw spindle with handwheel 60 and similar to the slide rest of a turning lathe.

After the treatment in the apparatus of FIG. 1, the strand is transferred to further processing in accordance with the invention, i.e. to equipment wherein the outer plastic layer 8 is applied so as to provide an intermediate or stock product as that illustrated in FIG. 1.

In the apparatus according to the invention, there may be arranged several support or guide sleeves corresponding to the sleeve 40 shown. Moreover, the functions and operating cycle of the apparatus can be controlled and operated automatically, herein included drawing in a strand section or segment between the collets 22 and 24 by rotating one of the reels 56, 58; tensioning the strand segment thus introduced by closing the clamping collets; movements of the grinding assembly during the grinding operation; release of the strand segment after the grinding by opening the clamping collets; and withdrawing the strand segment while simultaneously introducing a new strand segment in the apparatus by means of one of the reels 56, 58.

The reel support means 52, 54 or at least one thereof may therefore appropriately be provided with means for controlled advancing the strand by driven rotation of the reel in question. These advancing means may also simply be an appropriate crank handle.

The apparatus of the invention may also include a cutting tool similar to a turning tool whereby an initial machining of sheathing areas to be removed can be carried out prior to the grinding operation. The cutting tool can be mounted separately or can be arranged on the same displaceable mounting 44 as the grinding means 42.

Further variations from the embodiments represented in the drawings and described above may be contemplated without departing from the spirit of this invention, and the scope thereof should only be determined as limited by a proper interpretation of the terms used in the following claims.

What is claimed is:

1. A method of preparing a tubular product, in particular for making catheters, said tubular product including an inner plastic layer, an outer plastic layer, and a wire sheathing embedded there-between, the method comprising the steps of:
   applying said inner plastic layer onto a core wire as a plastic coating thereon,
   applying said wire sheathing onto said plastic coating as a continuous structure thereon,
   locally removing said wire sheating at spaced locations, thereby providing defined spaced curcumferential areas without said wire sheating and intermediate areas including said wire sheathing,
   applying said outer plastic layer over said spaced and intermediate areas, forming a structure intermittently reinforced with wire sheathing covered by said outer plastic layer,
   cutting said structure at one end of each of said defined spaced areas without said wire sheathing, and
   removing said core wire from said strand pieces to provide said tubular product.

2. The method of claim 1, wherein said step of locally removing the wire sheathing includes a grinding operation, while holding a length of said core wire with said plastic coating and said wire sheathing thereon, in a tensioned condition between two spaced clamping points.

3. A method of manufacturing an elongate stock product, in particular for further processing into catheters, said product including an inner plastic layer, an outer plastic layer, and a wire sheathing embedded therebetween, the method comprising the steps of:
   applying said inner plastic layer onto a core wire as a plastic coating thereon,
   applying said wire sheathing onto said plastic coating as a continuous structure thereon,
   locally removing said wire sheathing at spaced locations thereby providing defined spaced circumferential areas without wire sheathing and intermediate areas including said wire sheathing, and
   applying said outer plastic layer over said spaced and intermediate areas thereby forming said elongate stock, product as an elongated structure intermittently reinforced with the sheathing and covered by said outer plastic layer.

4. The method of claim 3, further comprising the step of winding up said elongated structure.

5. The method of claim 3, further comprising the steps of cutting said elongated structure at one end of each of said defined spaced areas without wire sheathing, thereby providing strand pieces, one end portion of each strand piece being without said wire sheathing, and removing said core wire from said strand pieces.

6. The method of claim 3 or 4, wherein said step of locally removing the wire sheathing includes a grinding operation, while holding a length of said core wire with said plastic coating and said wire sheathing thereon, in a tensioned condition between two spaced clamping points.

* * * * *